United States Patent [19]

Konz

[11] 4,059,594

[45] Nov. 22, 1977

[54] STEREOSPECIFIC PROCESS FOR PRODUCTION OF C-5-ARALKOXY-R-2-SUBSTITUTED-5-ALKYL-1,3-DIOXANES AND INTERMEDIATES

[75] Inventor: Marvin Joseph Konz, Lockport, N.Y.

[73] Assignee: FMC Corporation, Philadelphia, Pa.

[21] Appl. No.: 541,386

[22] Filed: Jan. 16, 1975

Related U.S. Application Data

[63] Continuation-in-part of Ser. No. 404,807, Oct. 9, 1973, abandoned, which is a continuation-in-part of Ser. No. 187,971, Oct. 12, 1971, abandoned.

[51] Int. Cl.$^2$ .................................. C07D 319/04
[52] U.S. Cl. .................................. 260/340.7; 71/88; 260/290 R; 260/294.9; 260/297 R; 260/329 R; 260/617 R
[58] Field of Search .................................. 260/340.7

[56] References Cited

U.S. PATENT DOCUMENTS 2,924,607  2/1960  Pattison .................. 260/340.7 X

FOREIGN PATENT DOCUMENTS 475,546  7/1951  Canada .................. 260/340.7

OTHER PUBLICATIONS

Craig et al., Journ. Org. Chem. 30, 12, pp. 4168–4175.
C.A. 64:4924e.
G. Dittus, Methoden Der Organ. Chemie (Houben-Weyl), Band VI/3, Sauerstoff Verbindungen I, Teil 3, 1965, pp. 442–446.
Payne, Tetrahedron, vol. 18, pp. 763–765 (1962).
Schwartz et al., Journ. Org. Chem., vol. 29, pp. 1976–1979, 1964.

Primary Examiner—Ethel G. Love
Attorney, Agent, or Firm—Harrison H. Young, Jr.; Henry R. Ertelt

[57] ABSTRACT

Production of c-5-aralkoxy-r-2-substituted-5-alkyl-1,3-dioxanes by epoxidizing the double bond of a 2-substituted-5-alkylidene-1,3-dioxane to form a cis epoxide, hydrogenolyzing said epoxide to form a 2-substituted-5-alkyl-5-hydroxy-1,3-dioxane in which there is a cis relationship between the 5-hydroxy and the 2-substituent, and etherifying said hydroxydioxane with an aralkyl halide.

4 Claims, No Drawings

STEREOSPECIFIC PROCESS FOR PRODUCTION OF C-5-ARALKOXY-R-2-SUBSTITUTED-5-ALKYL-1,3-DIOXANES AND INTERMEDIATES

This application is a continuation-in-part of my copending application Ser. No. 404,807, filed Oct. 9, 1973, now abandoned, the entire disclosure of which is incorporated herein by reference, which is a continuation-in-part of my application Ser. No. 187,971 filed Oct. 12, 1971, now abandoned.

This invention relates to the production of various substituted 1,3-dioxanes, including certain compounds which are highly active as herbicides. It also relates to novel intermediates and to novel stereospecific processes. It provides a new route for making herbicidally active cis isomers in high yields with little or no formation of inactive trans isomers.

One aspect of this invention relates to the production of 5-alkyl-5-arylmethoxy-1,3-dioxanes which have a 2-substituent that is in a cis-relationship to the 5-arylmethoxy group; that is, the 5-arylmethoxy group is in an axial configuration and the 2-substituent is in an equatorial configuration. Such compounds are particularly useful as herbicides and have much greater herbicidal activity than the corresponding isomers in which there is a trans rather than a cis relationship.

In the practice of this invention the starting material may be a 2-substituted-5-alkylidenedioxane having the structure

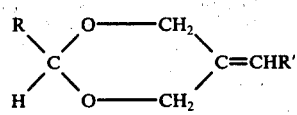

(which is conveniently produced, for example, from the corresponding 2-alkylidene-1,3-propanediol by a standard acetalization reaction with an aldehyde of the formula RCHO or by a standard transacetalization reaction with an acetal of such an aldehyde, e.g. $RCH(OC_2H_5)_2$).

The 2-substituted 5-alkylidene dioxane is epoxidized to form an epoxy compound of the general formula:

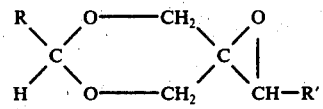

The epoxy compound may then be reduced, specifically hydrogenolyzed, to open the epoxide ring and produce the corresponding 2-substituted-5-hydroxy-5-alkyl-1,3-dioxane in which the 2-substituent and 5-hydroxy group are in cis relationship to each other. The 5-hydroxy group of the resulting compound is then etherified to form the desired 2-substituted-5-aralkoxy-5-alkyl-1,3-dioxane, as by reacting it with the corresponding aralkyl halide in the presence of a strong base.

The term "cis" is used herein, for convenience, to describe the epoxy 1,3-dioxanes in which there is a cis-relationship between the 5-oxygen atom and the substituent R. When such a cis relationship occurs the 5-oxygen atom is in an axial configuration and the 2-substituent is in an equatorial configuration. An indication of the steric configuration is given by the following sketches:

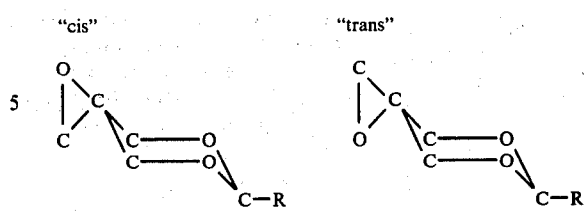

The cis epoxy compounds described above are not described in the literature. They may be distinguished readily from the corresponding trans epoxy compounds by the fact that, on hydrogenation with lithium aluminum hydride according to the method described in Example III A below, the pure cis epoxy compound is converted to the corresponding 2-substituted-5-hydroxy-5-alkyl-1,3-dioxane in which the content of the cis isomer (whose 2-substituent and 5-hydroxy group are in cis relationship) is at least three times the content, if any, of the trans isomer (whose 2-substituent and 5-hydroxy group are in trans relationship). The cis hydroxy compound, derived by hydrogenolysis of the cis epoxide, shows in highly diluted solution an infrared absorption characteristic of the intramolecular hydrogen bonding between the 5-hydroxy group and the oxygens of the dioxane ring and does not show an absorption characteristic of a free hydroxy group; the trans hydroxy compound shows a very strong absorption characteristic of a free hydroxy group. The cis epoxy compounds may also be identified by other analytical techniques such as nuclear magnetic resonance (nmr).

For the production of the cis epoxy compounds from the corresponding 2-substituted-2-alkylidene-1,3-dioxanes, a particularly suitable epoxidizing agent is that produced in situ from hydrogen peroxide and a nitrile such as benzonitrile (see Payne et. al., J. Org. Chem. 26, 659 (1961) and Payne, Tetrahendron 18, 763 (1962)). Other suitable nitriles are acetonitrile or other alkanenitrile such as propionitrile, butyronitrile, other nitriles having one or more -CN groups attached to hydrocarbon (which may carry one or more substituents which are inert under the reaction conditions) including dinitriles such as adiponitrile, benzonitriles such as benzonitrile itself or substituted benzonitriles (e.g. a halobenzonitrile such as any of the monochlorobenzonitriles). To avoid unnecessary consumption of peroxide the nitrile preferably is not one which is (like olefinic nitriles) subject to epoxidation under the reaction conditions. The concentration of hydrogen peroxide initially in the reaction mixture may be, for instance, in the range of about 2 to 30%, e.g. about 4 to 15% and the proportion of nitrile may be such as to provide about one nitrile group per molecular of hydrogen peroxide; the peroxide, in turn, is preferably used in amount of at least about one mol (e.g. about 1.1 to 1.3 moles) per mol of the olefinic dioxane. The epoxidation reaction is preferably carried out at a temperature within the range of about 0° to 40° C, more preferably about 5° to 20° C. The reaction mixture is preferably alkaline; to this end a buffer such as an alkali metal bicarbonate (or buffer of similar alkalinity) is present in the reaction mixture. It is usually preferable to carry out the epoxidation reaction in the presence of an inert diluent, such as an alcohol e.g. a lower alkanol, such as methanol or ethanol or isopropanol, or an ether-alcohol, such as a monoalkyl ether of ethylene glycol or of diethylene glycol (e.g., methyl cellosolve or ethyl carbitol or other water-soluble alcohol) or dioxane, and to add the hydrogen peroxide in the form of a solution thereof in such a diluent. Other epoxidizing agents which may be useful are m-chlorperbenzoic acid (see Schwartz and Blumbergs, J. Org. Chem. 29, 1976 (1964) and perbenzoic acid (see Favre and Gravel, Can. J. Chem. 41, 1452 (1963).

By the practice of this invention, it is possible to produce cis epoxides in high yields, with a minimum of the trans isomer, e.g. products are obtained which on hydrogenolysis yield the corresponding 5-hydroxy-5-methyl compound in which there is well over twice as much of the desired isomer (having the 2-substituent and the 5-hydroxy group in cis relationship) as of the other (trans) isomer, e.g., the ratio of these isomers is 4:1, 8:1 or even 15:1 or 70:1 or more.

It is noteworthy that when used to epoxidize 1-methylene-4-substituted-cyclohexanes (see Carlson and Behn, J. Org. Chem. 32, 1363 (1967)), the benzonitrile-hydrogen peroxide epoxidizing agent produced predominantly trans isomer rather than almost exclusively cis isomer as it is produced in my case.

The hydrogenolysis of the cis epoxide may be effected, if desired, by various methods, e.g., with lithium aluminum hydride, with sodium borohydride or by catalytic hydrogenation. Espeically good results are attained by the use of hydrogen (preferably under superatomspheric pressure) in the presence of a solid hydrogenation catalyst, particularly an active metal catalyst, such as palladium. When such a catalyst is ued it is found, surprisingly, that the cis epoxide is preferentially attacked with little or no attack on any trans epoxide and the 5-hydroxy product thus formed is richer in its desired cis form than the epoxide from which it is made. In place of palladium one may also use other metals known to act as catalysts for hydrogenations effected with elemental hydrogen under superatmospheric pressure, particularly metals of Group 8 of the periodic table such as platinum and Raney nickel. The hydrogenolysis agent must be one which causes splitting of an epoxide ring (having the oxygen attached to a tertiary carbon and to a primary or secondary carbon) at the bond between the oxygen and the Primary or secondary carbon. Preferably, the hydrogenolysis is effected with the epoxide dissolved in substantially non-acidic mediums, e.g., in a neutral solvent, such as alcohol or ether (e.g., ethanol, methanol, ethylcellosolve, methylcarbitol or dioxane), in contact with the solid catalyst. For the hydrogenolysis, suitable hydrogen pressures are, for instance, in the range of about 40 to 1000 psig using solutions in which the initial epoxide concentration is in the range of about 5 to 20% at temperatures in the range of about 10° to 100° C, e.g. about 20°–70° C.

It is found that in the hydrogenolysis step one may efficiently use the crude epoxide produced in the epoxidation step without the need for first isolating such epoxide. Thus, in an epoxidation process in which a carboxylic acid amide is formed (e.g. benzamide formed when the epoxidizing agent is a hydrogen peroxide-benzonitrile combination) the amide may be present in the hydrogenolysis step. It is particularly convenient and efficient to use the whole epoxidation reaction mixture, employing the same solvent (e.g. an alcohol, such as a lower alkanol, such as methanol) for both epoxidation and hydrogenolysis steps, as by simply adding the solid hydrogenation catalyst to that mixture and supplying thereto hydrogen under super-atmopsheric pressure. Generally (for safety, to avoid rapid evolution of oxygen when finely divided metal hydrogenation catalyst is added to the mixture) the hydrogen peroxide content of the mixture should be at a low level (e.g. below about 0.2%) prior to hydrogenolysis; such reduction can be effected by treatment with a small amount of an agent such as sodium sulfite which destroys residual hydrogen peroxide, or by maintaining the reaction mixture at an elevated temperature (e.g. at about 40° C, as for a period of about 2 hours) in the presence of a small amount of activated charcoal. Preferably, for best yields, the period between the conclusion of the epoxidation step and the commencement of hydrogenolysis is short (e.g. below 24 hours and preferably less than 8 hours); if the mixture is to be held more than a few hours before commencing hydrogenolysis, it is best to refrigerate it.

The etherification reaction may be conducted in conventional manner. For instance, one may use the known methods, such as Williamson type synthesis; see Kirk-Othmer, Encyclopedia of Chemical Technology, 2nd edition, Volume 8, pages 474–475. The aralkyl halide may be one of those commonly used for such reactions as chloride, bromide or iodide, for instance. The etherification reaction, per se, is well known as are other etherification (and esterification, etc.) reactions of a 5-hydroxy group on a 1,3-dioxane, and it is also within the broader scope of the invention to etherify, or esterify, or otherwise react the hydroxy group with other appropriate reactants.

The 2-substituted-5-hydroxy-5-alkyl-1,3-dioxanes of this invention are highly useful in that they provide a convenient route for the production of the corresponding 5-benzyloxy-5-alkyl compounds which, as mentioned above, are useful herbicides (e.g. for preemergence treatment to kill grassy weeds in soybean fields).

In the foregoing formulas R (the 2-substituent) may be the monovalent radical of an aldehyde having the formula R-CHO and having at least two carbon atoms (including the carbon of the -CHO group). Thus, for the production of preferred types of herbicidal compounds it may be alkyl, haloalkyl, aryl, aralkyl, aryloxyalkyl, cycloalkyl, arylalkoxyalkyl, alkoxyalkyl, or alkylsulfonylalkyl, where any aryl radical is phenyl or furyl which is unsubstituted or carries a single "X" substituent, where "X" is F, Cl, Br, lower alkyl, trifluoromethyl, lower alkoxy or benzyloxy. The R' substituent may be, for example, hydrogen or an organic radical of the type which is unaffected by the reagents used in the process, such as an alkyl or aryl radical.

In the aralkyl halide used for etherification the aryl portion may be a substituted or unsubstituted aromatic hydrocarbon radical or substituted or unsubstituted aromatic heterocyclic radical; in the preferred herbicidal compounds, this aryl portion is a monovalent aromatic phenyl, furyl, thienyl or pyridyl radical which is unsubstituted or has one, two or three (preferably less than three) "Y" substituents where Y is F, Cl, Br, CN, $CF_3$, lower alkyl or lower alkoxy.

The invention may also be used for compounds in which there are 2-substituents on the dioxane ring. Thus a ketone may be used in place of the aldehyde in the reaction with the 2-alkylidene-1,3-propanediol. The second 2-substituent on the 1,3-dioxane may be selected from the same group as those given above for R. Both substituents may constitute a single ring such as is produced by reacting cyclohexanone or cyclopentanone with the 2-alkylidene-1,3-propanediol. In the preferred herbicidal compounds of this invention the second 2-substituent, if any, is an alkyl radical or constitutes, with the first 2-substituent a single divalent radical forming the ring just described.

The alkyl radicals are preferable lower alkyl, and may be, for example, methyl, ethyl, propyl, isopropyl, n-butyl, isobutyl, sec-butyl, or t-butyl radicals; this preference applies whether the alkyl is present as such or as part of a combined radical as aralkyl, alkoxyalkyl or haloalkyl. The alkoxy, preferably lower alkoxy, radicals may, for example, be methoxy, ethoxy, propoxy, isopropoxy, butoxy, isobutoxy, sec-butyoxy or tert-butoxy radicals.

The following examples are given to illustrate this invention further. In the application all temperatures are in degrees centigrade, and all proportions are by weight unless otherwise indicated. In the examples pressures are atmospheric unless otherwise indicated; "reduced pressure" signifies, unless modified, the reduced pressure normally attainable using a water aspirator.

EXAMPLE I

A. Preparation of 2-methylene-1,3-propanediol

A mixture of 100 g of 2-methylene-1,3-dichloropropane and 121.62 of potassium carbonate in 800 ml of water was stirred and refluxed for 40 hours. The reaction mixture was concentrated by evaporation under reduced pressure to give a thick slurry which was extracted with four 100-ml portions of ethyl acetate. The extracts were filtered, combined, dried over $Na_2SO_4$ and concentrated under reduced pressure to an oil. Distillation of the oil gave 58.3 g of 2-methylene-1,3-propanediol, b.p. 68°–72°/0.24–0.25 mm Hg.

B. Preparation of 2-ethyl-5-methylene-1,3-dioxane

A mixture of 16.3 g of propionaldehyde and 20.2 g of 2-methylene-1,3-propanediol in 1200 ml of hexane containing 0.1 g p-toluenesulfonic acid was stirred thoroughly and the mixture was heated under reflux for two hours while 5.3 g of by-product water was collected in a Dean-Stark trap. The mixture was cooled, concentrated by evaporation under reduced pressure to 50 ml and then treated with 200 ml of ether. The ethereal solution was washed with 75 ml of ten percent sodium carbonate and two 75-ml portions of water, after which it was dried over $MgSO_4$ and concentrated to an oil. Distillation of the oil gave 21.5 g of 2-ethyl-5-methylene-1,3-dioxane, b.p. 68° C/41 mm Hg.

C. Preparation of 6-ethyl-1,5,7-trioxaspiro[2.5]octane

1. Using 30% hydrogen peroxide

A mixture of 5.0 g of 2-ethyl-5-methylene-1,3-dioxane 4.1 g of benzonitrile, 4.3 g of potassium bicarbonate and 25 ml of absolute methanol were stirred and the mixture was brought to 55°–60° C. Four ml of 30 percent aqueous hydrogen peroxide was added over a period of five hours. After addition, the reaction mixture was stirred at 55°–60° C for ½ hr., cooled and 75 ml of water was added. The aqueous solution was extracted with three 40-ml volumes of chloroform. Extracts were combined, washed with 40-ml of ten percent sodium carbonate and 40 ml of water, dried over $Na_2SO_4$ and concentrated by evapoation under reduced pressure to give a slurry. The slurry was filtered and the residue washed with ether. The combined filtrate and wash was concentrated to give 6.6 g of clear oil.

The reaction was repeated at 25° to give, after the same isolation procedure, 6.1 g of clear oil. The nmr spectrum of each oil indicated it to be a mixture containing cis and trans epoxides in which the cis isomer prodominated in a ratio of at least 19 to 1.

The two oils were combined and distilled to give 4.8 g of crude epoxide which distilled at 84°–95°/11 mm Hg. This crude product (4.4g) was combined with the product (10.2g) from a third preparation (run at 55°–60° using 10 g of methylenedioxane) and the mixture was distilled using a spinning band column to give 7.7 g of 6-ethyl-1,5,7-trioxaspiro[2.5]octane, b.p. 75°–90° C/11 mm Hg. A portion was redistilled using a jacketed Vigreux column to give colorless 6-ethyl-1,5,7-trioxaspiro[2.5]octane, b.p. 94°/10 mm Hg; $n_D^{25} = 1.4505$. The ir and nmr spectra were consistent with the assigned structure.

Analysis: Calc'd for $C_7H_{12}O_3$: C, 58.31; H, 8.39. Found: C, 58.60; H, 8.09.

2. Using 90% hydrogen peroxide

In a similar manner, a stirred mixture of 256 g of 2-ethyl-5-methylene-1,3-dioxane, 237 g of benzonitrile and 69 g of potassium bicarbonate in 1280 ml. of methanol was cooled to 15° C. To the mixture was added dropwise during 3 hours, maintaining the temperature of 15°–20° C, a solution of 86.8 g of 90% aqueous hydrogen peroxide in 640 ml. of methanol. The reaction mixture was stirred at room temperature for approximately 20 hours. Vapor phase chromatographic analysis indicated 91% conversion of the olefin to epoxide. The mixture was then heated at 40°–45° for 3 hours, then cooled to 25°–30° and 20 ml. of saturated sodium sulfite solution was added to destroy residual peroxide. The solvent was removed by evaporation under reduced pressure. The slurry thus obtained was diluted with one liter of ethyl ether and filtered. The filter cake was washed with 750 ml. of ethyl ether and the ether solutions combined and dried over magnesium sulfate. The ether was removed from the dried solution by evaporation under reduced pressure to give 310 g of product which was found by vapor phase chromatographic analysis to contain 71.6% of 6-ethyl-1,5,7-trioxaspiro[2.5]octane, the principal impurity being benzamide. The nmr spectrum of this product indicated the cis content to be greater than 90%. The epoxydioxane, containing benzamide, was hydrogenolyzed without further purification.

D. Preparation of r-2-ethyl-c-5-hydroxy-5-methyl-1,3-dioxane

A solution of 7.6 g of 6-ethyl-1,5,7-trioxaspiro-[2.5]octane in 75 ml. of ethanol was hydrogenated for 1 hour at 45 psig initial hydrogen pressure at 25° in a low-pressure, shaking hydrogenation apparatus using 1.5 g of ten percent palladium on charcoal as catalyst. During the hydrogenation, the hydrogen pressure was reduced five pounds. The ethanolic solution was filtered and concentrated by evaporation under reduced pressure to obtain an oil which was dissolved in 100 ml. of ether. The etheral solution was washed with three 20 ml. portions of water, dried over $MgSO_4$ and concentrated to give 3.6 g of an oil. The aqueous washes were combined, saturated with sodium chloride and extracted with three 50 ml. portions of ether; etheral extracts were combined, dried over $MgSO_4$ and concentrated to give an additional 2.6 g of oil. Oils were combined (6.2 g) and distilled to give 6.0 g of r-2-ethyl-c-5-hydroxy-5-methyl-1,3-dioxane, b.p. 61°–63° C/10 mm Hg; $n_D^{25} = 1.4378$. The ir and nmr spectra of the products were consistent with the assigned structure.

Analysis: Calc'd for $C_7H_{14}O_3$: C, 57.51; H, 9.65. Found: C, 57.80; H, 9.39.

E. Preparation of c-5-benzyloxy-r-2-ethyl-5-methyl-1,3-dioxanes

1. r-2-Ethyl-c-5-(2-methylbenzyloxy-5-methyl-1,3-dioxane

Two grams of a 54.7% suspension of sodium hydride in mineral oil was stirred with 75 ml. of hexane, the solid allowed to settle and the hexane drawn off. The washing was repeated and finally 75 ml. of dimethylformamide was added to the sodium hydride. To this suspension was added slowly during 0.75 hour, a solution of 5.9 g of r-2-ethyl-c-5-hydroxy-5-methyl-1,3-dioxane in 25 ml. of dimethylformamide. The mixture was stirred at ambient temperature for 1.5 hours and to it was added 6.2 g of 2-methylbenzyl chloride. The reaction mixture was heated at 90°–95° for 21 hours and then concentrated by distillation under reduced pressure (about 11 mm) to a volume of about 60 ml. The hot residue was poured into 250 g of ice and the aqueous mixture was stirred until the ice was melted. The cold mixture was filtered and the filtrate was extracted four times with 100-ml. portions of diethyl ether. The extracts were combined, dried over $MgSO_4$ and concentrated by distillation under reduced pressure to obtain 9.8 g of yellow liquid. The liquid was found by nmr to contain dimethylformamide thus the liquid was dissolved in 175 ml. of diethyl ether, the solution was washed with water, dried over $MgSO_4$ and concentrated by evaporation under reduced pressure to obtain 8.4 g of amber liquid. Distillation of this liquid through a short-path distillation apparatus, then through a spinning-band column gave 4.8 g of r-2-ethyl-c-5-(2-methylbenzyloxy)-5-methyl-1,3-dioxane, b.p. 69.5°–72°/0.14 mm Hg; $n_D^{25}$ 1.5075. The ir and nmr spectra was consistent with the assigned structure.

Analysis: Calc'd for $C_{15}H_{33}O_3$: C, 71.97; H, 8.86. Found: C, 72.66; H, 8.09.

2. c-5-(2-Chlorobenzyloxy)-r-2-ethyl-5-methyl-1,3-dioxanes

By the method described above, r-2-ethyl-c-5-hydroxy-5-methyl-1,3-dioxane was reacted with 2-chlorobenzyl chloride to yield c-5-(2-chlorobenzyloxy)-r-2-ethyl-5-methyl-1,3-dioxane, b.p. 102°–104° 0.0002 mm Hg. $n_D^{25}$ 1.5186. The ir and nmr spectra were consistent with the assigned structure.

Analysis: Calc'd for $C_{14}H_{19}ClO_3$: C, 62.11; H, 7.07. Found: C, 62.01; H, 7.34.

EXAMPLE II

A. Preparation of 2-chloromethyl-5-methylene-1,3-dioxane

A mixture of 5.3 of 2-methylene-1,3-propanediol, 6.7 g of chloroacetaldehyde dimethyl acetal and 0.05 g of p-toluenesulfonic acid was heated and stirred until distillation of by-product methanol ceased. The crude product was dissolved in 100 ml. of benzene and the benzene solution was washed with two 30-ml. portions of aqueous sodium carbonate and two 30-ml. portions of water. The washed solution was dried over $MgSO_4$ and distilled under reduced pressure to obtain 4.8 g of colorless liquid, b.p. 81°–87°/14 mm Hg; $n_D^{24}$ 1.4734. Redistillation gave 3.9 g of 2-chloromethyl-5-methylene-1,3-dioxane, b.p. 78°–79°/13 mm Hg; $n_D^{24}$ 1.4746. The ir and nmr spectra were consistent with the assigned structure.

Analysis: Calc'd for $C_6H_9ClO_2$: C, 48.49; H, 6.11. Found: C, 48.68: H, 6.06.

Repetition of the above procedure using 15 g of 2-methylene-1,3-propanediol per run gave 15.6 g and 14.3 g of pure 2-chloromethyl-5-methylene-1,3-dioxanes in two successive runs.

Another repetition using 15 g of 2-methylene-1,3-propanediol gave, after removal of the benzene from the washed and dried solution, 24.1 g of amber liquid, the nmr of which showed it to be essentially pure 2-chloromethyl-5-methylene-1,3-dioxane. This amber liquid was found satisfactory for use in the epoxidation reaction without further purification.

B. Preparation of 6-Chloromethyl-1,5,7-trioxaspiro[2.5]octane

1. Using 30% hydrogen peroxide

By the method of Example IC (Procedure 1), a mixture of 10.0 g of 2-chloromethyl-5-methylene-1,3-dioxane, 7.2 g of benzonitrile and 7.4 g of potassium bicarbonate in 50 ml. of methanol was treated dropwise with 8 ml. of 30% aqueous hydrogen peroxide during 6 hours at 55°–60°. The reaction mixture was treated as in IC to obtain 5.8 g of colorless liquid, $n_D^{24}$ 1.4809. The nmr spectrum showed the product to be 6-chloromethyl-1,5,7-trioxaspiro[2.5]octane of which at least 95% was the desired cis isomer.

2. Using m-chloroperbenzoic acid

A mixture of 16.7 g of m-chloroperbenzoic acid (85%) in 200 ml. of chloroform was added during 15 minutes to a solution of 13.0 g of 2-chloromethyl-5-methylene-1,3-dioxane in 25 ml. of chloroform. The reaction mixture was heated under reflux with stirring for 16 hours. The mixture was cooled to 10° and excess m-chloroperbenzoic acid decomposed by dropwise addition of 10% sodium sulfite solution until an iodide test was negative for peroxide. The organic layer was washed with 10% sodium bicarbonate solution (3 × 100 ml.) followed by 100 ml. of saturated sodium chloride solution and dried over sodium sulfate. The dry solution was concentrated by evaporation under reduced pressure to obtain 12.8 g of pale yellow liquid. The liquid was distilled using a short-path distillation apparatus to obtain three fractions totalling 9.3 g of colorless liquid which distilled at a column temperature of 115°–124° under 13 mm. The nmr showed this product to be a mixture of 7 parts of the cis isomer and 3 parts of the trans isomer.

Redistillation of the final fraction (3.9 g) using a jacketed Vigreux column gave 1.8 g of colorless liquid, b.p. 53°–59°/0.01 mm.; $n_D^{25}$ 1.4799. The ir and nmr spectra of this liquid showed it to be the pure 6-chloromethyl-1,5,7-trioxaspiro-[2.5]octane having the desired cis relationship between the epoxide oxygen and the chloromethyl group.

Analysis: Calc'd for $C_6H_9ClO_3$: C, 43.78; H, 5.51. Found: C, 43.62; H, 5.46.

C. Preparation of r-2-chloromethyl-c-5-hydroxy-5-methyl-1,3-dioxane

Hydrogenation of the 5.8 g of 6-chloromethyl-1,5,7-trioxaspiro[2.5]octane. Prepared as in Example IIB, method 1, was carried out as described in Example ID. The pressure drop during 1.5 hours was 2.5 psig. The mixture was filtered and the filtrate was concentrated by evaporation under reduced pressure to obtain 4.7 g of colorless liquid, the nmr spectrum of which showed no epoxide remaining and no trans hydroxy compound. Distillation of the liquid through a short-path distillation apparatus gave 3.7 g of r-2-chloromethyl-c-5-hydroxy-5-methyl-1,3-dioxane, b.p. 46°–47°/0.01 mm Hg, $n_D^{25}$ 1.4667.

Analysis: Calc'd for $C_6H_{11}ClO_3$: C, 43.25; H, 6.66. Found: C, 43.12; H, 6.63.

D. Preparation of c-5-benzyloxy-r-2-chloromethyl-5-methyl-1,3-dioxanes

1. r-2-Chloromethyl-c-5-(2-fluorobenzyloxy)-5-methyl-1,3-dioxane

A suspension of 0.8 g of sodium hydride in 75 ml. of toluene was prepared as described in Example IE, procedure 1 and to it was added during 0.5 hour 5.1 g of r-2-chloromethyl-c-5-hydroxy-5-methyl-1,3-dioxane. The mixture was stirred for 1 hour at 25°–30° and to it was added 4.5 g of 2-fluorobenzyl chloride. The mixture was heated under reflux for 3 hours, then allowed to stand at room temperature for 16 hours. The reaction mixture was washed with water (3×30 ml.), the washes extracted with toluene (2×30 ml.) and the toluene solutions combined. After drying over $MgSO_4$, the toluene solution was concentrated by evaporation under reduced pressure to give 5.8 g of oil. Distillation gave 0.7 g of r-2-chloromethyl-c-5-(2-fluorbenzyloxy)-5-methyl-1,3-dioxane which was recrystallized from petroleum ether to give crystals which melted at 30°. The ir and nmr spectra were consistent with the assigned structure.

EXAMPLE III

A. Preparation of c-5-hydroxy-r-2-isopropyl-5-methyl-1,3-dioxane

A solution of 5.0 g of 6-isopropyl-1,5,7-trioxaspiro[2.5]octane, m.p. 57°–62° prepared by epoxidation of 2-isopropyl-5-methylene-1,3-dioxane, in 100 ml. of dry ether was added during 1 hour to a well-stirred suspension of 2.1 g of lithium aluminum hydride in 275 ml. of dry ether. The mixture refluxed during the addition and was maintained under reflux for two hours after addition was completed. Excess hydride was decomposed by addition of 20 ml. of ethyl acetate while cooling the mixture. Water (100ml.) was added and the solid isolated on a filter. The solid was washed with ethyl ether (3×25 ml.) and the ether washes added to the filtrate. The ether extracts were separated, dried over $MgSO_4$ and concentrated by evaporation under reduced pressure to give an oil. Distillation gave 1.9 g of pure c-5-hydroxy-r-2-isopropyl-5-methyl 1,3-dioxane, b.p. 25°/0.003 mm Hg; $n_D^{24}$ 1.4406. The nmr and ir spectra were consistent with the assigned structure and showed no trans isomer present. The ir spectrum of a very dilute solution of the compound in carbon tetrachloride showed a very sharp band at 3585 cm$^{-1}$ characteristic of intramolecular hydrogen bonding and did not show the band characteristic of the free hydroxyl group, thus establishing the cis relationship between the hydroxy group and the isopropyl group.

Analysis: Calc'd for $C_8H_{16}O_3$: C, 59.98; H, 10.07. Found: C, 60.16; H, 10.32.

EXAMPLE IV 1.7 g of 90% aqueous hydrogen peroxide was mixed with 13 ml of absolute methanol and the resulting methanol solution of hydrogen peroxide was added to a stirred mixture of 5 g of 2-ethyl-5-methylene-1,3-dioxane, 2.1 g of acetonitrile, 1.0 g of potassium bicarbonate and 28 ml of absolute methanol while the latter mixture was maintained at a temperature of 25°. Stirring at 25° was continued for 20 hours and the mixture was then heated at 45°–50° for 4 hours, after which it was cooled and 2.5 ml of saturated aqueous sodium sulfite solution was added to decompose residual hydrogen peroxide. The mixture was filtered and the solvent was removed by evaporation under reduced pressure. The slurry thus obtained was mixed with 100 ml of ethyl ether, filtered, dried over magnesium sulfate, after which the ether was removed from the resulting solution by evaporation under reduced pressure to give 3.8 g of clear colorless oil. Analysis by vpc indicates that this oil contains about 11% of unreacted 2-ethyl-5-methylene-1,3-dioxane and about 89% 6-ethyl-1,5,7-trioxaspiro [2.5] octane, the latter being substantially all cis.

EXAMPLE V 30.5 g of 90% aqueous hydrogen peroxide was mixed with 240 ml of absolute methanol and the resulting methanol solution of hydrogen peroxide was added dropwise over a period of 22 minutes to a stirred mixture of 100 g of 2-ethyl-5-methylene-1,3-dioxane, 92.5 g of benzonitrile, 17.9 g of potassium bicarbonate and 450 ml of absolute methanol while the latter mixture was maintained at a temperature of 22°–23°. Stirring at 20°–25° was continued for 21 hours and the mixture was then heated at 45° for 3 hours, after which 5 ml of saturated aqueous sodium sulfite solution was added to decompose residual hydrogen peroxide. The solvent was removed by evaporation under reduced pressure. The slurry thus obtained was filtered (the solids being principally benzamide) and the filtrate was taken up in 500 ml of ethyl ether, dried over magnesium sulfate and filtered, after which the ether was removed from the resulting solution by evaporation under reduced pressure to give 112 g of clear colorless oil. NMR analysis indicates that this oil contains about 20% aromatic compound (mixture of benzonitrile and benzamide) dissolved in the 6-ethyl-1,5,7-trioxaspiro [2.5] octane, the cis:trans ratio in the latter being about 96:4. The crude oil was hydrogenolyzed without further purification by mixing 50 g thereof with 175 ml of absolute ethanol and 5 g of 10% palladium on carbon in a lowpressure, shaking hydrogenation apparatus and hydrogenating for 70 minutes at 45 psig initial hydrogen pressure and 25° initial temperature; after the first 35 minutes of hydrogenation the hydrogen pressure had fallen to 20 psig and the temperature was 45°; after the second 35 minutes the hydrogen pressure was 19 psign and the temperature was 25°. The reaction mixture was filtered and the solvent removed from the filtrate to give 44.1 g of clear colorless liquid. The nmr spectrum of the liquid was consistent with the structure, r — 2 — ethyl — c — 5 — hydroxy — 5 — methyl — 1,3 — dioxane containing about 11% aromatic compound as impurity.

EXAMPLE VI

The procedure described in Example I.C.2 was followed except that the aqueous 90% hydrogen peroxide was not premixed with part of the methanol but was added directly (over a 2½ to 3 hour period) to the stirred mixture of the other ingredients, containing about 75% methanol by weight, while the reaction mixture was maintained at 8° C. The stirred reaction mixture was allowed to warm up gradually to room temperature (20°-25°) and allowed to stand at that temperature overnight; measurements indicated that about 0.05% residual peroxide was present (calculated as $H_2O_2$). Three liters of the reaction mixture was then directly mixed with 35 g of 5% palladium on carbon catalyst and poured into an autoclave, which was sealed, purged with hydrogen and then maintained under a constant pressure of 150 psig of hydrogen while stirring at 50° C during 3 hours of hydrogenation. The resulting reaction mixture was filtered, the filter cake being washed twice with 100 ml portions of methanol. The filtrate (including washings) was then subjected to reduced pressure (20 mm Hg absolute) at 50° C to flash off methanol. The residual slurry containing precipitated benzamide was filtered. The filter cake was slurried with 500 ml of ethyl ether; the slurry filtered and the ether treatment repeated. The three filtrates were combined, the ether removed under reduced pressure and the project was recovered by fractional distillation.

EXAMPLE VII

Example VI is repeated except that acetonitrile was substituted for benzonitrile, again using about one mol of nitrile per mole of $H_2O_2$ and a stoichiometric excess of nitrile and $H_2O_2$, e.g. a 20-30% excess.

Among the herbicidal compounds which may be produced in accordance with this invention are the following:

r-2-ethyl-c-5-(2-fluorobenzyloxy)-5-methyl-1,3-dioxane, m.p. 74.5°-75°;

c-5-benzyloxy-r-2-bromomethyl-5-methyl-1,3-dioxane, m.p. 55°-56°;

c-5-benzyloxy-r-2-chloromethyl-5-methyl-1,3-dioxane, m.p. 50°-51°;

r-2-chloromethyl-5-methyl-c-5-(2-methylbenzyloxy)-1,3-dioxane, m.p. 57°-58°;

c-5-(2-chlorobenzyloxy)-r-2-chloromethyl-5-methyl-1,3-dioxane, m.p. 53°-54°;

c-5-benzyloxy-r-2-isopropyl-5-methyl-1,3-dioxane, b.p. 92°-96°/0.1 mm;

c-5-benzyloxy-5-methyl-r-2-propyl-1,3-dioxane, b.p. 99.5°-100.5°/0.01 mm;

c-5-(2-chlorobenzyloxy)-5-methyl-r-2-propyl-1,3-dioxane. b.p. 112°-114°/0.045 mm;

5-methyl-c-5-(2-methylbenzyloxy)-r-2-propyl-1,3-dioxane, b.p. 107°-109°/0.015 mm;

c-5-(2-bromobenzyloxy)-5-methyl-r-2-propyl-1,3-dioxane, b.p. 118°-120°/0.05 mm;

c-5-benzyloxy-5-ethyl-r-2-propyl-1,3-dioxane, b.p. 112°-114°/5×10$^{-3}$ mm;

5-ethyl-c-5-(2-methylbenzyloxy)-r-2-propyl-1,3-dioxane, b.p. 117°-117.5°/1×10$^{-3}$ mm;

c-5-(2-chlorobenzyloxy)-5-ethyl-r-2-propyl-1,3-dioxane, b.p. 127°-128°/1×10$^{-3}$ mm;

5-ethyl-c-5-(2-fluorobenzyloxy)-r-2-propyl-1,3-dioxane, b.p. 107°-109.5°/0.015-0.020 mm;

c-5-(2-bromobenzyloxy)-5-ethyl-r-2-propyl-1,3-dioxane, b.p. 142°-145°/0.015 mm;

c-5-(2-fluorobenzyloxy)-r-2-isopropyl-5-methyl-1,3-dioxane, b.p. 95°-98°/0.1 mm;

c-5-benzyloxy-r-2-isopropyl-5-methyl-1,3-dioxane, b.p. 92°-96°/0.1 mm;

r-2-isopropyl-5-methyl-c-5-(2-methylbenzyloxy)-1,3-dioxane, b.p. 108°-110°/0.02 mm;

c-5-(2-chlorobenzyloxy)-r-2-isopropyl-5-methyl-1,3-dioxane, b.p. 116°-118°/0.025 mm;

c-5-benzyloxy-5-ethyl-r-2-isopropyl-1,3-dioxane, b.p. 98°-100°/1×10$^{-3}$ mm;

5-ethyl-c-5-(2-fluorobenzyloxy)-r-2-isopropyl-1,3-dioxane, b.p. 97°-99°/0.075 mm;

5-ethyl-r-2-isopropyl-c-5-(2-methylbenzyloxy)-1,3-dioxane, b.p. 110°-112°/0.05 mm;

c-5-(2-chlorobenzyloxy)-5-ethyl-r-2-isopropyl-1,3-dioxane, b.p. 117°-118.5/0.05 mm;

c-5-(2-bromobenzyloxy)-5-ethyl-r-2-isopropyl-1,3-dioxane, b.p. 121°-123.5°/1×10$^{-3}$ mm;

c-5-benzyloxy-5-methyl-r-2-(1-methylpropyl)-1,3-dioxane, b.p. 99°-102°/2.5×10$^{-3}$ mm;

c-5-(2-chlorobenzyloxy)-5-methyl-r-2-(1-methylpropyl)-1,3-dioxane, b.p. 108°-110°/0.015 mm;

5-methyl-c-5-(2-methylbenzyloxy)-r-2-(1-methylpropyl)-1,3-dioxane, b.p. 96°-99.5/1.4×10$^{-3}$ mm;

c-5-(2-fluorobenzyloxy)-5-methyl-r-2-(1-methylpropyl)-1,3-dioxane, b.p. 90°-92°/2×10$^{-3}$ mm;

c-5-(2-bromobenzyloxy)-5-methyl-r-2-(1-methylpropyl)-1,3-dioxane, b.p. 127°-129°/0.02 mm;

c-5-benzyloxy-5-methyl-r-2-(2-methylpropyl)-1,3-dioxane, b.p. 101°14 103.5°/0.02 mm;

c-5-(2-chlorobenzyloxy)-5-methyl-r-2-(2-methylpropyl)-1,3-dioxane; b.p. 117°-119.5°/0.01 mm;

c-5-(fluorobenzyloxy)-5-methyl-r-2-(2-methylpropyl)-1,3-dioxane, b.p. 102°-104.5°/0.01 mm;

5-methyl-c-5-(2-methylbenzyloxy)-r-2-(2-methylpropyl)-1,3-dioxane, m.p. 34.8-36.5°;

c-5-(2-bromobenzyloxy)-5-methyl-r-2-(2-methylpropyl)-1,3-dioxane, b.p. 115°-118°/0.058 mm;

c-5-benzyloxy-r-2-(1-ethylpropyl)-5-methyl-1,3-dioxane, b.p. 109°-109.5°/0.059 mm;

c-5-(2-chlorobenzyloxy)-r-2-(1-ethylpropyl)-5-methyl-1,3-dioxane, b.p. 108°-110°/4×10$^{-3}$ mm;

r-2-(1-ethylpropyl)-5-methyl-c-5-(2-methylbenzyloxy)-1,3-dioxane, b.p. 100°-108.5/8×10$^{-3}$ mm;

r-2-(1-ethylpropyl)-c-5-(2-fluorobenzyloxy)-5-methyl-1,3-dioxane, b.p. 96°-99.5°/0.01 mm.

Particularly suitable herbicidal compounds are those in which there is a Y substituent in the 2-position of the benzyloxy radical, e.g. r-2-isopropyl-5-methyl-c-5-(2-methylbenzyloxy)-1,3-dioxane, c-5-(2-chlorobenzyloxy)-r-2-isopropyl-5-methyl-1,3-dioxane, c-5-(2-chlorobenzyloxy)-5-methyl-r-2-propyl-1,3-dioxane, and 5-methyl-c-5-(2-methylbenzyloxy)-r-2-propyl-1,3-dioxane.

The materials are very useful for the control and elimination of grassy plants, particularly annual grasses, in the presence of broadleaved crops, such as cotton, sugar beets, peanuts, soy beans, snap beans, lima beans, tomatoes or nursery stock, particularly by preemergence treatment of such grassy weeds. They are effective in low dosages such as in the range of one-fourth to 10 pounds of active component per acre.

For herbicidal applications, the active compounds may be utilized in diverse formulations, including the agricultural adjuvants and agricultural carriers, i.e. those materials normally employed to facilitate the dispersion of active ingredients in agricultural applications, recognizing the fact that the formulation and mode of application of a toxicant may affect the activity of the material in a given application. Thus, the compound of this invention may be formulated as a granule of relatively large particle size, as a wettable powder, as an emulsifiable concentrate, as a solution, or as any of several other known types of formulations depending on the desired mode of application.

Granular formulations are particularly useful for aerial distribution or for penetration of a canopy of foliage. Useful granular formulations may be of several types. Impregnated granules are those wherein the active ingredient is applied to large particles of an absorbent carrier, such as an attapulgite or kaolin clay, corncobs, expanded mica, etc., normally in the form of a solution in a solvent. Surface-coated granules may be produced by spraying the molten active ingredient onto the surface of a generally nonabsorbent particle or by spraying on a solution of active ingredient in a solvent. The core may be water-soluble such as a prilled fertilizer, or insoluble such as sand, marble chips or coarse talc. Particularly useful is a granule wherein a wettable powder is applied as a surface coating to a sand or other insoluble particle such that the wettable may be dispersed on contact of the granule with moisture. Granules may be produced by agglomeration of dusts or powders by compaction rollers, by extrusion through a die or by use of a granulating disc. Granular formulations may vary widely in concentration, with useful formulations containing as little as 0.5% or as much as 95% of active ingredient.

Wettable powders, also useful formulations for both pre- and post-emergence herbicides, are in the form of finely divided particles which disperse readily in water or other dispersants. The wettable powder is ultimately applied to the soil either as a dry dust or as an emulsion in water or other liquid. Typical carriers for wettable powders include fuller's earth, kaolin clays, silicas and other highly absorbent, readily wet inorganic diluents. Wettable powders normally are prepared to contain about 5% to 80% of active ingredient, depending on the absorbency of the carrier, and usually also contain a small amount of a wetting, dispersing or emulsifying agent to facilitate dispersion. For example, a useful wettable powder formulation contains 80.8 parts of a 5-benzyloxy-5-methyl-1,3-dioxane 17.9 parts of palmetto clay, and 1.0 part of sodium lignosulfonate and 0.3 part of sulfonated aliphatic polyester as wetting agents.

Other useful formulations for herbicidal applications are the emulsifiable concentrates, which are homogeneous liquid or paste compositions dispersible in water or other dispersant, and may consist entirely of the compound of this invention with a liquid or solid emulsifying agent, or may also contain an agriculturally acceptable liquid carrier, such as xylene, heavy aromatic naphthas, isophorone and other nonvolatile organic solvents.

Typical wetting, dispersing or emulsifying agents used in agricultural formulations include, for example, the alkyl and alkylaryl sulfonates and sulfates and their sodium salts; polyethylene oxides; sulfonated oils; fatty acid esters of polyhydric alcohols; and other types or surface-active agents, many of which are available in commerce. The surface-active agent, when used, normally comprises from 1% to 15% by weight of the herbicidal composition.

These formulations may be applied without further dilution or as dilute solutions, emulsions or suspensions in water or other suitable diluent. The compositions may be applied to the area wherein control is desired by spraying onto the undesired vegetation or onto the surface of the soil in the case of liquid compositions or by distribution from mechanical equipment in the case of solids. The surface-applied material may also be blended into the upper layer of soil by cultivation, or left as applied, as is appropriate to gain the optimum results with the particular treatment.

The active herbicidal compound of this invention may be formulated and/or applied with insecticides, fungicides, nematicides, plant-growth regulators, fertilizers, and other agricultural chemicals. In applying the active compound of this invention, whether formulated alone or with other agricultural chemicals, an effective amount and concentration of 5-benzyloxy-5-methyl-1,3-dioxane of course employed.

It is apparent that various modifications may be made in the formulation and application of the novel compound of this invention, without departing from the inventive concept herein, as defined in the following claims:

I claim:
1. A hydroxy-1,3-dioxane of the formula:

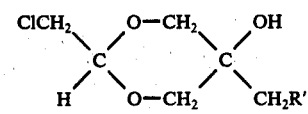

in which R' is hydrogen or lower alkyl.
2. A hydroxy-1,3-dioxane as in claim 1 in which R' is hydrogen.
3. A hydroxy-1,3-dioxane of the formula:

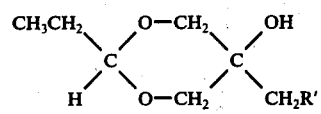

in which R' is hydrogen or lower alkyl, at least 60% of said hydroxy-1,3-dioxane being in the form in which there is a cis-relationship between the 5-hydroxy and the 2-ethyl.
4. An epoxy-1,3-dioxane of the formula:

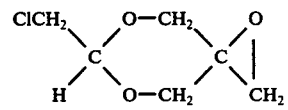

in which at least 60% of said epoxy-1,3-dioxane is in the form in which there is a cis-relationship between the epoxide oxygen and the 2-chloromethyl.

* * * * *